(12) United States Patent
Bryant, II (10) Patent No.: US 9,830,428 B2
(45) Date of Patent: Nov. 28, 2017

(54) SYSTEMS AND METHODS FOR FITNESS REPORTING USING PAYMENT CARDS

(71) Applicant: MasterCard International Incorporated, Purchase, NY (US)

(72) Inventor: Dexter E. Bryant, II, Saint Charles, MO (US)

(73) Assignee: Mastercard International Incorporated, Purchase, NY (US)

( * ) Notice: Subject to any disclaimer, the term of this patent is extended or adjusted under 35 U.S.C. 154(b) by 504 days.

(21) Appl. No.: 14/497,739

(22) Filed: Sep. 26, 2014

(65) Prior Publication Data

US 2016/0092654 A1    Mar. 31, 2016

(51) Int. Cl.
*G06Q 20/34*    (2012.01)
*G06F 19/00*    (2011.01)

(52) U.S. Cl.
CPC ......... *G06F 19/3481* (2013.01); *G06Q 20/34* (2013.01)

(58) Field of Classification Search
CPC .................................................... G06Q 20/34
USPC ........................................................ 705/44
See application file for complete search history.

(56) References Cited

U.S. PATENT DOCUMENTS

| | | | |
|---|---|---|---|
| 7,661,588 B2 * | 2/2010 | Porvaznik | G01C 22/006 235/105 |
| 8,237,702 B2 | 8/2012 | Chang | |
| 2010/0201393 A1 | 8/2010 | Quercia et al. | |
| 2011/0217681 A1 | 9/2011 | Krejcarek | |
| 2014/0214674 A1 | 7/2014 | Narula | |

FOREIGN PATENT DOCUMENTS

CN    103148863 A    6/2013

* cited by examiner

*Primary Examiner* — Jessica L Lemieux
(74) *Attorney, Agent, or Firm* — Armstrong Teasdale LLP (57) ABSTRACT

A computer-implemented method for tracking fitness data of a cardholder by using a fitness payment card and a fitness tracking computing device is provided. The method includes storing registration data, wherein the registration data includes an account identifier associated with the fitness payment card and the cardholder. The method also includes receiving, by the fitness tracking computing device, a fitness data transfer message that includes the registration data and fitness data of the cardholder, wherein the fitness data is collected by the fitness payment card. The method further includes determining that the fitness payment card is registered in a fitness tracking program based on the registration data. The method also includes electronically generating a fitness report including at least the fitness data of the cardholder and providing the fitness report to the cardholder.

18 Claims, 9 Drawing Sheets

FIG. 9

# SYSTEMS AND METHODS FOR FITNESS REPORTING USING PAYMENT CARDS

BACKGROUND

The field of the disclosure relates generally to the use of payment cards configured to track and report fitness data of a cardholder associated with the payment card, and more particularly, to a fitness payment card having a fitness-tracking component and the ability to report fitness data to a payment network.

At least some known merchants accept electronic payment transactions as an alternative to cash for the payment for goods and services. In such electronic payment transactions, a payment card may be used. Examples of payment cards include credit cards, debit cards, charge cards, store-value cards, gift cards, and pre-paid cards, as well as other types of cards. At least some known cards are uniquely tied to a consumer or cardholder account that is backed by a card-issuing lending institution or bank.

In today's society, maintaining a healthy lifestyle is important to many people. Oftentimes, people use fitness tracking devices to collect appropriate fitness data (e.g., steps taken, distance traveled, calories burned, etc.) and monitor their fitness as part of a healthy lifestyle. At least some known fitness devices are carried (or worn) by the user of the device and are used throughout the day or while exercising. In some cases, it may be difficult or undesirable to use such devices, and often these devices are configured solely to track fitness data. It would be beneficial to allow a person to monitor his or her fitness using a device he or she already carries on a regular basis.

BRIEF DESCRIPTION OF THE DISCLOSURE

In one aspect, a computer-implemented method for tracking fitness data of a cardholder using a fitness payment card and a fitness tracking computing device in communication with a memory is provided. The method includes storing registration data within the memory, wherein the registration data includes an account identifier associated with the fitness payment card and the cardholder. The method also includes receiving, by the fitness tracking computing device, a fitness data transfer message that includes the registration data and fitness data of the cardholder, wherein the fitness data is collected by the fitness payment card. The method further includes determining that the fitness payment card is registered in a fitness tracking program based on the registration data. The method still further includes electronically generating a fitness report including at least the fitness data of the cardholder. The method also includes providing the fitness report to the cardholder.

In another aspect, a computer system for tracking fitness data of a cardholder is provided. The computer system includes a memory and a fitness tracking computing device. The fitness tracking computing device is configured to store registration data within the memory, wherein the registration data includes an account identifier associated with a fitness payment card and the cardholder. The fitness tracking computing device is also configured to receive a fitness data transfer message that includes the registration data and fitness data of the cardholder, wherein the fitness data is collected by the fitness payment card. The fitness tracking computing device is further configured to determine that the fitness payment card is registered in a fitness tracking program based on the registration data. The fitness tracking computing device is still further configured to electronically generate a fitness report including at least the fitness data of the cardholder and to provide the fitness report to the cardholder.

In yet another aspect, computer-readable media having computer-executable instructions embodied thereon is provided. When executed by at least one processor, the computer-executable instructions cause the processor to store registration data within a memory, wherein the registration data includes an account identifier associated with a fitness payment card and a cardholder. The computer-executable instructions further cause the processor to receive a fitness data transfer message that includes the registration data and fitness data of the cardholder, wherein the fitness data is collected by the fitness payment card. The computer-executable instructions further cause the processor to determine that the fitness payment card is registered in a fitness tracking program based on the registration data. The computer-executable instructions further cause the processor to electronically generate a fitness report including at least the fitness data of the cardholder and to provide the fitness report to the cardholder.

In yet another aspect, a fitness payment card for tracking fitness data of a cardholder for use in an electronic payment transaction is provided. The fitness payment card includes a fitness tracking component, a processing device, and a wireless communication device configured to receive and transmit at least one of registration data, transaction data, and fitness data of the cardholder.

DETAILED DESCRIPTION OF THE DISCLOSURE

The following detailed description illustrates embodiments of the disclosure by way of example and not by way of limitation. It is contemplated that the embodiments have general application to processing financial transaction data by a third party in industrial, commercial, and residential applications.

As used herein, an element or step recited in the singular and proceeded with the word "a" or "an" should be understood as not excluding plural elements or steps, unless such exclusion is explicitly recited. Furthermore, references to "one embodiment" of the present disclosure are not intended to be interpreted as excluding the existence of additional embodiments that also incorporate the recited features.

The systems and methods described herein are directed to using a fitness payment card configured to track and report fitness of a cardholder. There are at least some known fitness devices that are carried (or worn) by a user, that are used throughout the day or while exercising to track fitness data of the device user. In some cases, it may be difficult or undesirable to use such devices. These devices are not normally carried by the user, but rather are solely configured to track fitness data. A solution would be to allow a person to monitor his or her fitness using a device he or she already carries on a regular basis, for example, a fitness payment card enrolled in a fitness tracking program. The technical effect of the systems and methods described herein is to address the technical problems of these known systems.

The technical effect of the disclosure is achieved by: (i) storing registration data within a memory, wherein the registration data includes an account identifier associated with the fitness payment card and a cardholder; (ii) receiving, by a fitness tracking computing device, a fitness data transfer message that includes the registration data and fitness data of the cardholder, wherein the fitness data is collected by the fitness payment card; (iii) determining that the fitness payment card is registered in a fitness tracking program based on the registration data; (iv) electronically generating a fitness report including at least the fitness data of the cardholder; and (v) providing the fitness report to the cardholder.

Cardholders having fitness payment cards (e.g., a payment card such as a credit card, a debit card, or a prepaid card that is configured with the fitness functionality described herein and that is enrolled in a fitness tracking program) will be able to initiate transactions with merchants while at the same time fitness data is communicated with the payment network. Transaction data associated with these payment transactions are received and processed over a payment network for processing the payment transactions. The transaction data include, among other data points, data associated with the cardholder and the merchant involved in the payment transaction. As explained below in further detail, the fitness data collected by the fitness payment card as part of the fitness tracking program is also communicated to the payment network for further processing. The fitness data can be communicated with the payment network as part of processing a payment transaction or separate from payment transaction processing. The fitness tracking program may also offer at least one incentive to the cardholder(s) enrolled in the fitness tracking program based at least on the fitness data of the cardholder. The incentive may be offered, for example, to the cardholder(s) for taking at least a threshold number of steps or travelling at least a threshold distance. The incentive may include, for example, a coupon, at least one rewards points, or an advertisement.

Figure 1:
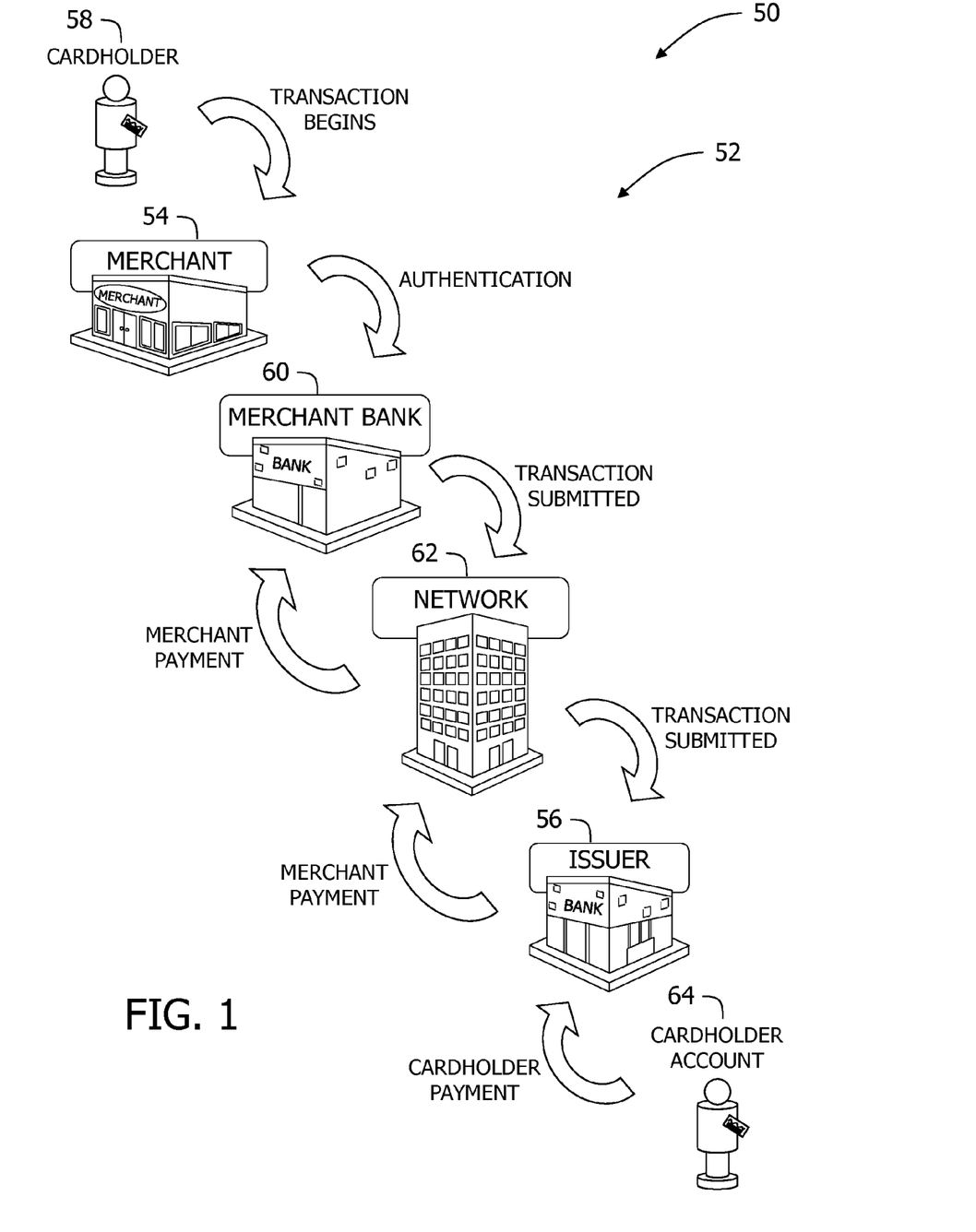
FIG. 1 is a schematic diagram illustrating an example multi-party payment card industry system for enabling payment-by-card transactions, including transactions initiated using a fitness payment card in accordance with the present disclosure.

FIG. 1 is a schematic diagram 50 illustrating an example multi-party payment card industry system 52 for enabling payment-by-card transactions in which a merchant 54 and a card issuer 56 do not necessarily have a one-on-one relationship. The payment-by-card transactions include transactions initiated with a fitness payment card as described herein. The methods and systems described herein relate to a payment card system, such as a credit card payment system using the MasterCard® interchange. The MasterCard® interchange is a proprietary communications standard promulgated by MasterCard International Incorporated® for the exchange of financial transaction data between financial institutions that are members of MasterCard International Incorporated®. (MasterCard is a registered trademark of MasterCard International Incorporated located in Purchase, N.Y., U.S.A.).

Payment processing system, such as system 52, may utilize a variety of different types of payment cards, including the fitness payment cards described herein, offered as payment by the consumer. Payment cards, also referred to herein as financial transaction cards or fitness payment cards, can refer to, for example, credit cards, debit cards, and prepaid cards. These cards can all be used as a method of payment for performing a transaction. As described herein, the term "financial transaction card" or "payment card" includes cards such as credit cards, debit cards, and prepaid cards, but also includes any other devices that may hold payment account information, such as mobile phones, personal digital assistants (PDAs), and key fobs.

In the payment card system, a financial institution called the "issuer" 56 issues a payment card, such as a credit card, more particularly, a fitness payment card, to a cardholder 58, who uses the fitness payment card to tender payment for a purchase from merchant 54. To accept payment with the fitness payment card, merchant 54 must normally establish an account with a financial institution that is part of the financial payment system. This financial institution is usually called the "merchant bank" 60 or the "acquiring bank" or "acquirer bank."When cardholder 58 tenders payment for a purchase with the fitness payment card, merchant 54 requests authorization from merchant bank 60 for the amount of the purchase. The request may be performed over telephone, but is usually performed through the use of a POS terminal (not shown in FIG. 1). The authorization request may further include fitness data captured on the fitness payment card. POS terminal reads the payment card identification information from, for example, a magnetic stripe on the fitness payment card or a wireless communication device within the fitness payment card, and communicates electronically with the transaction processing computers of merchant bank 60. Alternatively, merchant bank 60 may authorize a third party (not shown in FIG. 1) to perform transaction processing on its behalf. In this case, a POS terminal of the merchant 54 will be configured to communicate with the third party. Such a third party is usually called a "merchant processor" or an "acquiring processor."

Using an interchange network 62, the computers of merchant bank 60 or the merchant processor will communicate with the computers of issuer bank 56 to determine whether the cardholder's account is in good standing and whether the purchase is covered by the cardholder's available credit line. Based on these determinations, the request for authorization will be declined or accepted. If the request for authorization is accepted, an authorization code is issued to merchant 54 via an authorization response message.

In the case of a credit card, when a request for authorization is accepted, the available credit line of cardholder's account 64 is decreased. Normally, a charge is not posted immediately to the cardholder's account because bankcard associations have promulgated rules that do not allow merchant 54 to charge, or "capture," a transaction until goods are shipped or services are delivered. When merchant 54 ships or delivers the goods or services, merchant 54 captures the transaction by, for example, appropriate data entry procedures on a POS terminal. If the cardholder cancels a transaction before it is captured, a "void" is generated. If the cardholder returns goods after the transaction has been captured, a "credit" is generated.

After an electronic payment transaction is captured, the transaction is settled between merchant 54, merchant bank 60, and issuer 56. Settlement refers to the transfer of financial data or funds between a transaction account of merchant 54, merchant bank 60, and issuer 56 related to the transaction. Usually, transactions are captured and accumulated into a "batch," which are settled as a group.

In one embodiment, payment processing systems may also utilize a fitness payment card configured to provide payment card data and fitness data to a POS terminal through use of a wireless system. The wireless system may include, but is not limited to, a radio frequency identification (RFID) system, a cellular communication system, a Bluetooth® communication system, a near-field communication (NFC) system, or any other suitable wireless communication system that allows payment processing systems to function as described herein. (Bluetooth is a trademark of Bluetooth SIG, Inc. of Bellevue, Wash., U.S.A.). For example, the RFID system may include an RFID device within the payment card and an RFID reader positioned within a POS terminal. In this embodiment, the fitness payment card wirelessly transmits payment card data to the POS terminal in order to initiate the payment transaction. The fitness payment card may also wirelessly transmit fitness data to the POS terminal for further processing by network 62.

Figure 2:
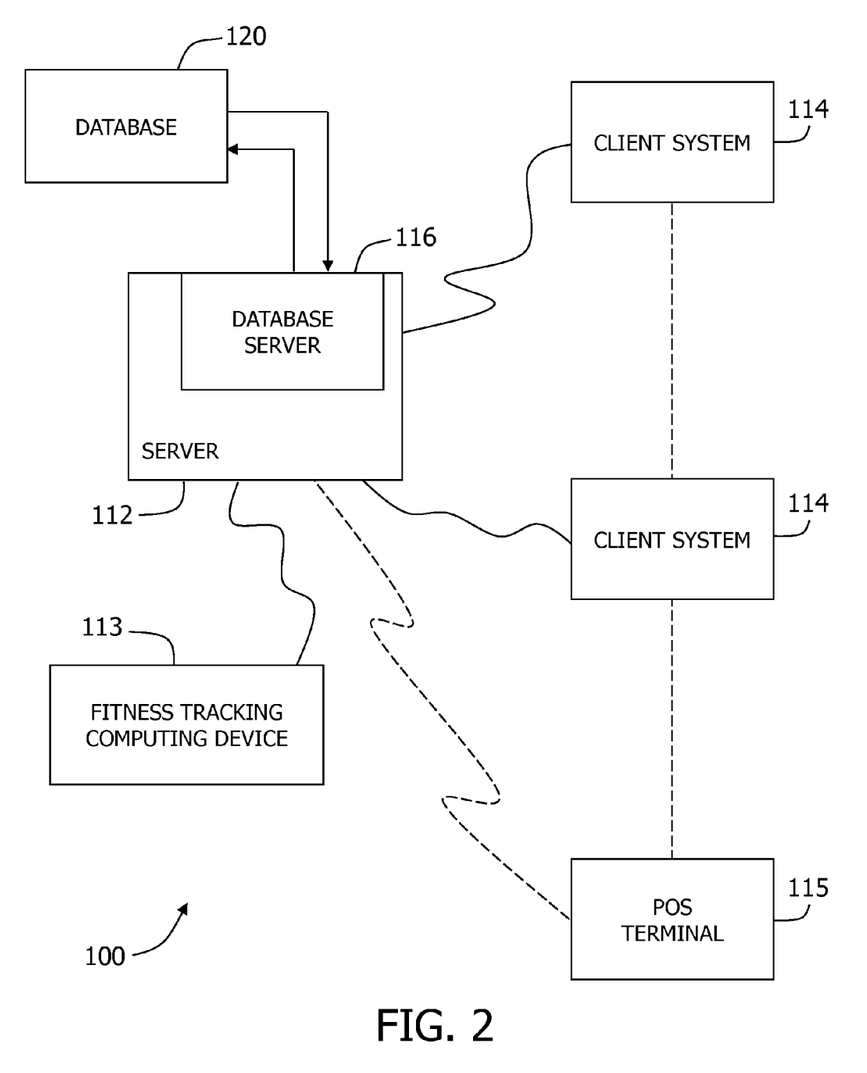
FIG. 2 is a simplified block diagram of an example computer system for processing payment-by-card transactions, including transactions initiated using a fitness payment card, in accordance with one embodiment of the present disclosure.

FIG. 2 is a simplified block diagram of an example embodiment of a payment card system 100 for processing payment-by-card transactions including transactions initiated using a fitness payment card. Payment card system 100 may be utilized by account holders as part of a process of initiating an authorization request and transaction, as well as initiating a fitness data transfer message, as described below.

More specifically, in the example embodiment, system 100 includes a server system 112, and a plurality of client sub-systems, also referred to as client systems 114, connected to server system 112. System 100 further includes fitness tracking computing device 113. Fitness tracking computing device 113 can be in communication with or, alternatively, integral to server system 112. In one embodiment, client systems 114 are computers including a web browser, such that server system 112 is accessible to client systems 114 using the Internet. In another embodiment, client systems 114 are smart phones including web access, either through a web browser or through a client application, such that server system 112 is accessible to client systems 114 using the Internet. Client systems 114 may be associated with a user or consumer, for example cardholder 58. Client systems 114 may alternatively be associated with merchant 54 or issuer 56. Client systems 114 may be interconnected to the Internet through a variety of interfaces including a network, such as a local area network (LAN) or a wide area network (WAN), dial-in connections, cable modems and special high-speed ISDN lines. Client systems 114 could be any device capable of interconnecting to the Internet including a web-based phone, also referred to as smart phone, personal digital assistant (PDA), tablets, or other web-based connectable equipment. In the example embodiment, fitness tracking computing device 113 (which includes any computing device programmed to perform as described herein) is configured to process fitness data transfer messages and/or electronic payment authorization request or response messages, including fitness data and/or transaction data associated with such fitness data transfer messages. Accordingly, fitness tracking computing device 113 may be in communication with or an integral part of server system 112.

System 100 also includes a point-of-sale (POS) terminal 115, which is connected to client systems 114 and may be connected to server system 112 and/or fitness tracking computing device 113. POS terminal 115 may be interconnected to the Internet through a variety of interfaces including a network, such as a local area network (LAN) or a wide area network (WAN), dial-in connections, cable modems, wireless modems, cellular communications, and special high-speed ISDN lines. POS terminal 115 may be any device capable of interconnecting to the Internet and of reading information from a consumer's financial transaction card. Although illustrated as including one POS terminal 115, system 100 may include any number of POS terminals 115 and operate as described herein.

A database server 116 is connected to database 120, which contains information on a variety of matters, as described below in greater detail. In one embodiment, centralized database 120 is stored on server system 112 and can be accessed by potential users at one of client systems 114 by logging onto server system 112 through one of client systems 114. In an alternative embodiment, database 120 is stored remotely from server system 112 and may be non-centralized. Database 120 may store transaction data generated as part of sales activities conducted over the payment card system 100 including data relating to merchants, account holders or consumers, and purchases. Database 120 may also store registration data, which includes at least an account identifier associated with the fitness payment card and a cardholder. Database 120 may also store fitness data gathered by a fitness payment card and provided to server 112 though, for example, fitness computing device 113.

In the example embodiment, one of client systems 114 may be associated with an acquirer, for example, merchant bank 60 (shown in FIG. 1), while another one of client systems 114 may be associated with an issuer, for example, issuer 56 (shown in FIG. 1). Yet another client one of client systems 114 may be associated with a consumer, for example, cardholder 58 (shown in FIG. 1). Furthermore, POS terminal 115 may be associated with merchant 54, and server system 112 may be associated with interchange network 62.

Figure 3:
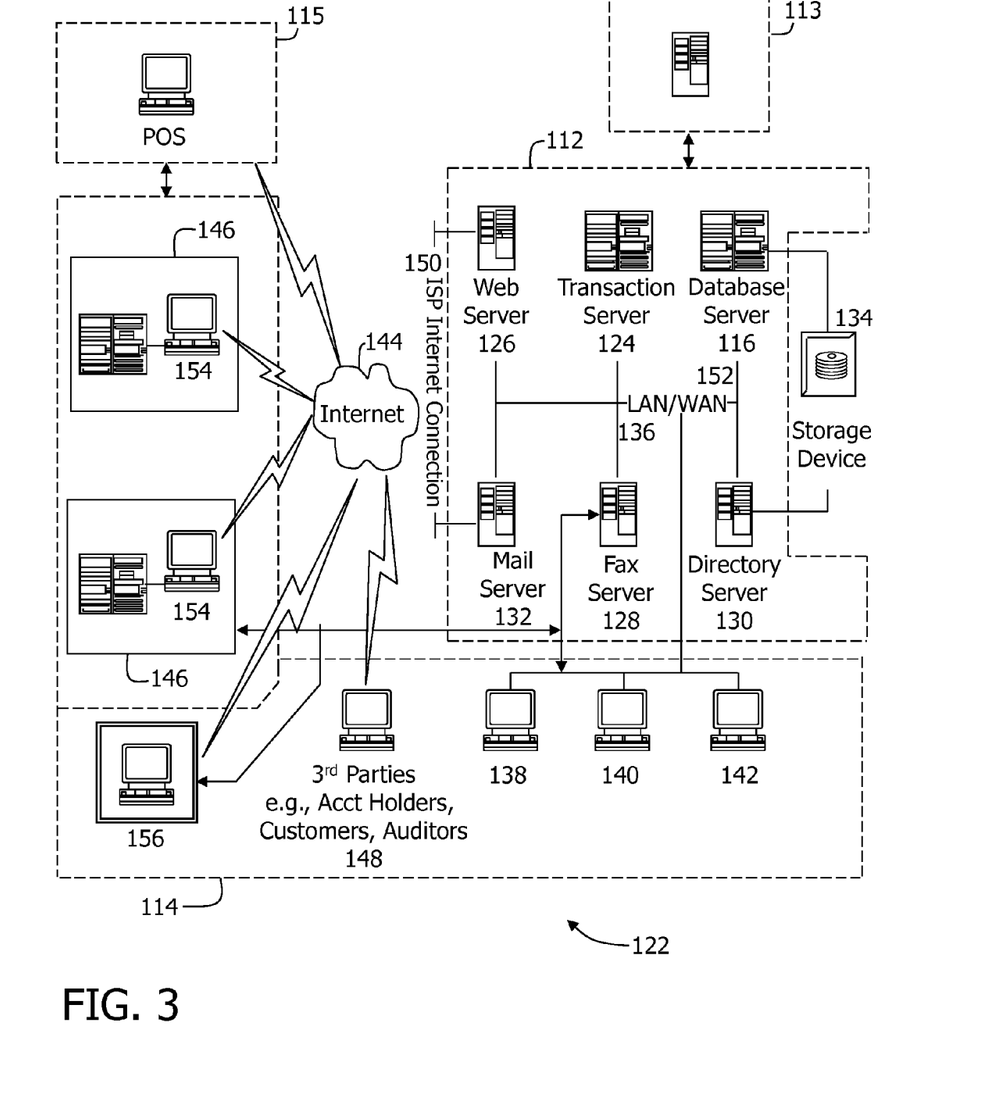
FIG. 3 is an expanded block diagram of an example embodiment of a server architecture of a computer system for processing payment-by-card transactions, including transactions initiated using a fitness payment card, in accordance with one embodiment of the present disclosure.

FIG. 3 is an expanded block diagram of an example embodiment of a server architecture of a payment card system 122 for processing payment-by-card transactions including transactions initiated using a fitness payment card. Components in system 122, identical to components of system 100 (shown in FIG. 2), are identified in FIG. 3 using the same reference numerals as used in FIG. 2. System 122 includes server system 112, fitness tracking computing device 113, client systems 114, and POS terminal 115. Server system 112 further includes database server 116, an application server 124, a web server 126, a fax server 128, a directory server 130, and a mail server 132. A disk storage unit 134 (i.e., a storage device) is coupled to database server 116 and directory server 130. Disk storage unit 134 may be configured to store a database, for example, database 120 (shown in FIG. 2). Servers 116, 124, 126, 128, 130, and 132 are coupled in a local area network (LAN) 136. In addition, a system administrator's workstation 138, a user workstation 140, and a supervisor's workstation 142 are coupled to LAN 136. Alternatively, workstations 138, 140, and 142 are coupled to LAN 136, for example, using an Internet 144 link or are connected through an Intranet.

Each workstation, 138, 140, and 142 is a personal computer or other client device having a web browser. Although the functions performed at the workstations typically are illustrated as being performed at respective workstations 138, 140, and 142, such functions can be performed at one of many personal computers coupled to LAN 136. Workstations 138, 140, and 142 are illustrated as being associated with separate functions only to facilitate an understanding of the different types of functions that can be performed by individuals having access to LAN 136.

Server system 112 is configured to be communicatively coupled to various individuals, including employees 146 and to third parties, e.g., account holders, consumers, auditors, etc., 148 using an ISP Internet connection 150. The communication in the example embodiment is illustrated as being performed using Internet 144, however, any other wide area network (WAN) type communication can be utilized in other embodiments, i.e., the systems and processes are not limited to being practiced using Internet 144. In addition, and rather than WAN 152, local area network 136 could be used in place of WAN 152.

In the example embodiment, any authorized individual having a workstation 154 can access system 122. At least one of the client systems includes a manager workstation 156 located at a remote location. In the example embodiment, workstations 154 and 156 are personal computers having a web browser. Also, workstations 154 and 156 are configured to communicate with server system 112. Furthermore, fax server 128 communicates with remotely located client systems, including client system 114 using a telephone link. Fax server 128 is configured to communicate with other workstations 138, 140, and 142 as well.

As used herein, the terms "software" and "firmware" are interchangeable, and include any computer program stored in memory for execution by personal computers, workstations, clients and servers, including RAM memory, ROM memory, EPROM memory, EEPROM memory, and non-volatile RAM (NVRAM) memory. The above memory types are example only, and are thus not limiting as to the types of memory usable for storage of a computer program.

Figure 4:
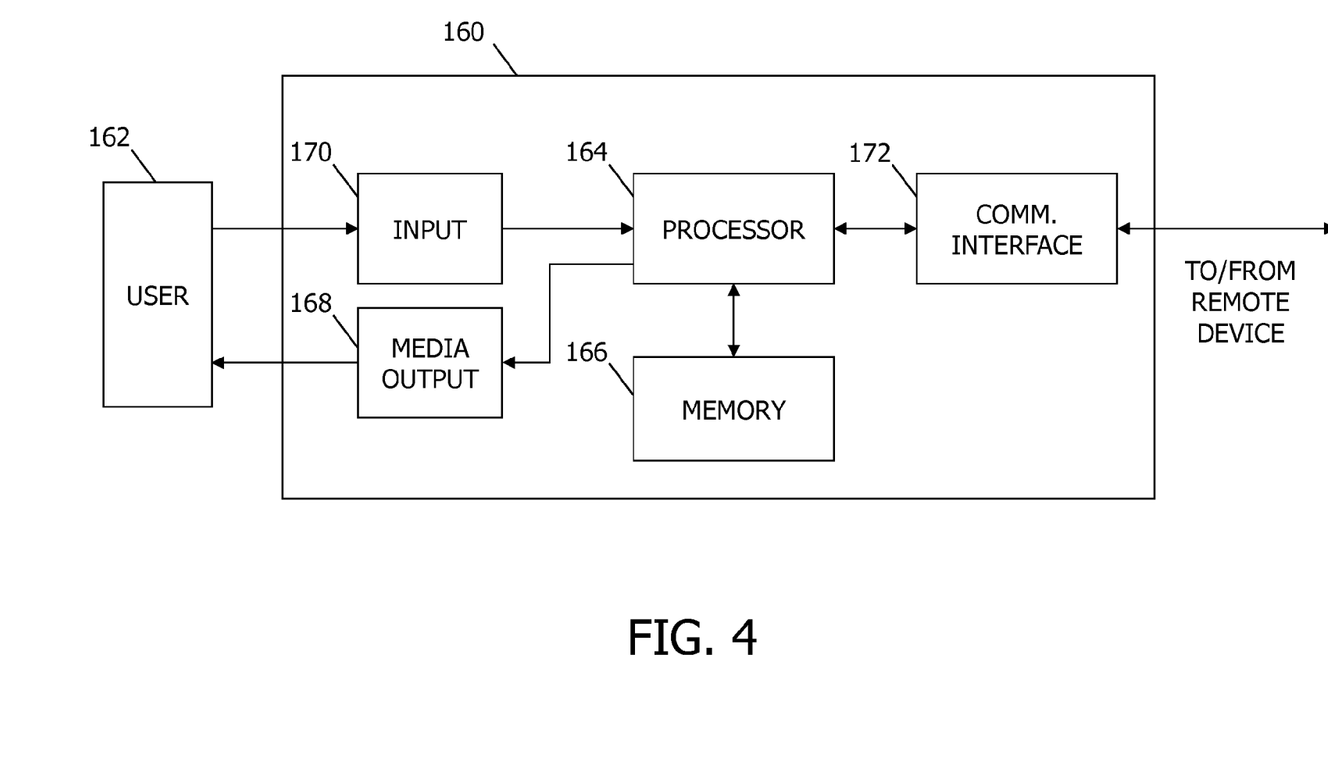
FIG. 4 illustrates an example configuration of a client device shown in FIGS. 2 and 3.

FIG. 4 illustrates an example configuration of a client device 160 operated by a user 162. Client device 160 may include, but is not limited to, client systems 114, 138, 140, and 142, POS terminal 115, workstation 154, and manager workstation 156 (shown in FIG. 3).

Client device 160 includes a processor 164 for executing instructions. In some embodiments, executable instructions are stored in a memory area 166. Processor 164 may include one or more processing units (e.g., in a multicore configuration). Memory area 166 is any device allowing information such as executable instructions and/or written works to be stored and retrieved. Memory area 166 may include one or more computer readable media.

Client device 160 also includes at least one media output component 168 for presenting information to user 162. Media output component 168 is any component capable of conveying information to user 162. In some embodiments, media output component 168 includes an output adapter such as a video adapter and/or an audio adapter. An output adapter is operatively coupled to processor 164 and operatively couplable to an output device such as a display device (e.g., a liquid crystal display (LCD), organic light emitting diode (OLED) display, or "electronic ink" display) or an audio output device (e.g., a speaker or headphones).

In some embodiments, client device 160 includes an input device 170 for receiving input from user 162. Input device 170 may include, for example, a keyboard, a pointing device, a mouse, a stylus, a touch sensitive panel (e.g., a touch pad or a touch screen), a gyroscope, an accelerometer, a position detector, or an audio input device. A single component such as a touch screen may function as both an output device of media output component 168 and input device 170.

Client device 160 may also include a communication interface 172, which is communicatively couplable to a remote device such as server system 112 (shown in FIG. 3). Communication interface 172 may include, for example, a wired or wireless network adapter or a wireless data transceiver for use with a mobile phone network (e.g., Global System for Mobile communications (GSM), 3G) or other mobile data network (e.g., Worldwide Interoperability for Microwave Access (WIMAX)).

Stored in memory area 166 are, for example, computer readable instructions for providing a user interface to user 162 via media output component 168 and, optionally, receiving and processing input from input device 170. A user interface may include, among other possibilities, a web browser and client application. Web browsers enable users, such as user 162, to display and interact with media and other information typically embedded on a web page or a website from server system 112. A client application allows user 162 to interact with a server application from server system 112.

In some embodiments, user 162 uses client device 160 to access a web browser or client application at the user interface of the client device 160. Client device 160 may include POS terminal 115. User 162 may use POS terminal 115 to perform a transaction (as described above) using a fitness payment card (not shown in FIG. 4), wherein during the transaction, fitness data captured at the fitness payment card is sent over the payment card processing system 62 (shown in FIG. 1) in a fitness data transfer message. In other embodiments, client device 160 may include client system 114. User 162 may use client device 160 to register for a fitness tracking program, optionally offered by a payment company through a payment network. User 162 may use client device 160 to send registration information to a fitness tracking computing device 113, wherein registration information includes at least an account identifier associated the fitness payment card and the user, for example, a cardholder. User 162 may use client system 114 to send fitness data captured at the fitness payment card over the payment card processing system, absent a transaction. User 162 may initiate a fitness data transfer message using the web browser or client application, wherein the fitness data transfer message includes at least registration data and the fitness data collected by the fitness payment card.

Figure 5:
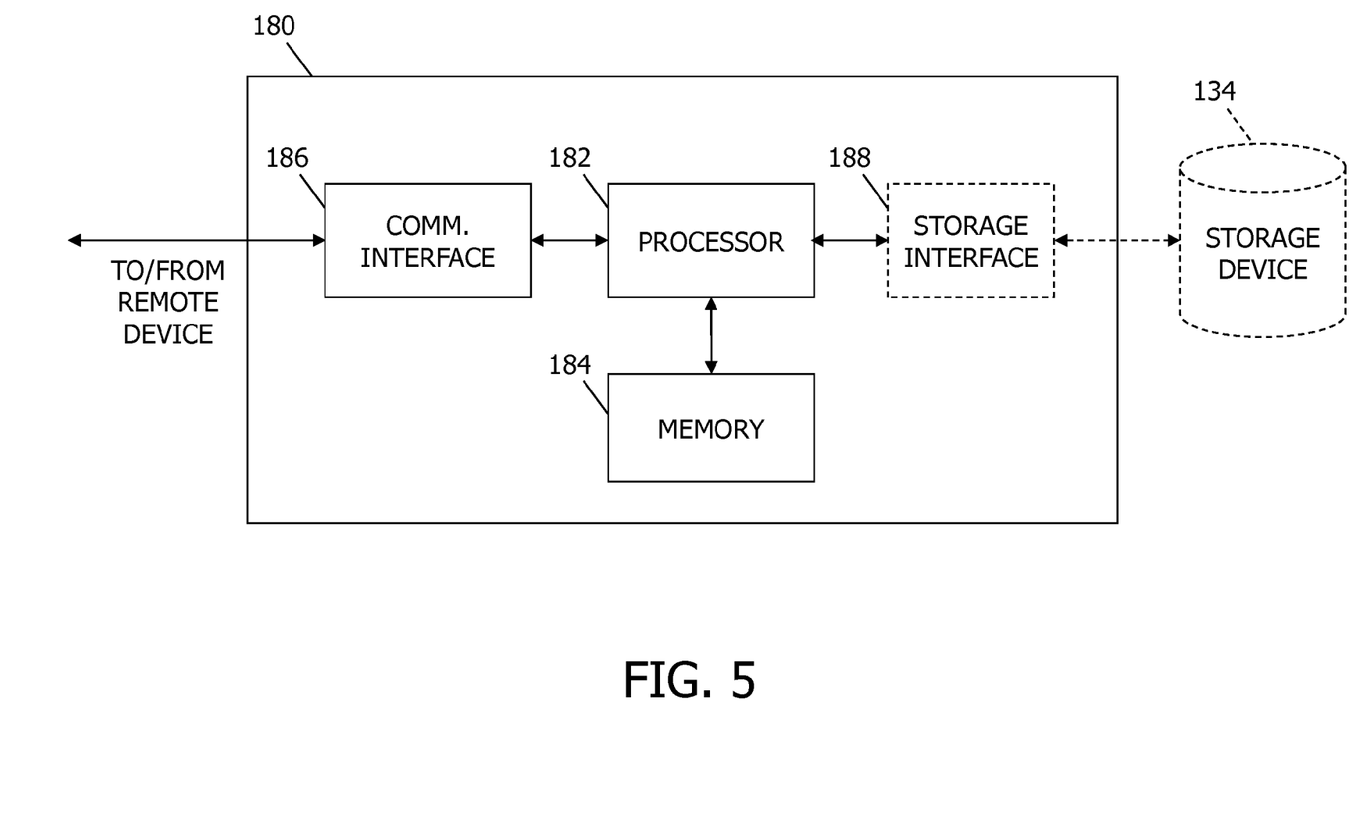
FIG. 5 illustrates an example configuration of a server system shown in FIGS. 2 and 3.

FIG. 5 illustrates an example configuration of a server computing device 180 such as fitness tracking computing device 113 and/or server system 112 (shown in FIG. 3). Server computing device 180 may include, but is not limited to, fitness tracking computing device 113, database server 116, application server 124, web server 126, fax server 128, directory server 130, mail server 132, and any other computing device configured to function as described herein.

Server computing device 180 also includes a processor 182 for executing instructions. Instructions may be stored in a memory area 184, for example. Processor 182 may include one or more processing units (e.g., in a multicore configuration).

Processor 182 is operatively coupled to a communication interface 186 such that server computing device 180 is capable of communicating with a remote device such as client device 160 (shown in FIG. 4) or another server computing device 180. For example, communication interface 186 may receive requests from client system 114 via the Internet, as illustrated in FIG. 3.

Processor 182 may also be operatively coupled to storage device 134. Storage device 134 is any computer-operated hardware suitable for storing and/or retrieving data. In some embodiments, storage device 134 is integrated in server computing device 180. For example, server computing device 180 may include one or more hard disk drives as storage device 134. In other embodiments, storage device 134 is external to server computing device 180 and may be accessed by a plurality of server computing devices 180. For example, storage device 134 may include multiple storage units such as hard disks or solid state disks in a redundant array of inexpensive disks (RAID) configuration. Storage device 134 may include a storage area network (SAN) and/or a network attached storage (NAS) system.

In some embodiments, processor 182 is operatively coupled to storage device 134 via a storage interface 188. Storage interface 188 is any component capable of providing processor 182 with access to storage device 134. Storage interface 188 may include, for example, an Advanced Technology Attachment (ATA) adapter, a Serial ATA (SATA) adapter, a Small Computer System Interface (SCSI) adapter, a RAID controller, a SAN adapter, a network adapter, and/or any component providing processor 182 with access to storage device 134.

Figure 6A:
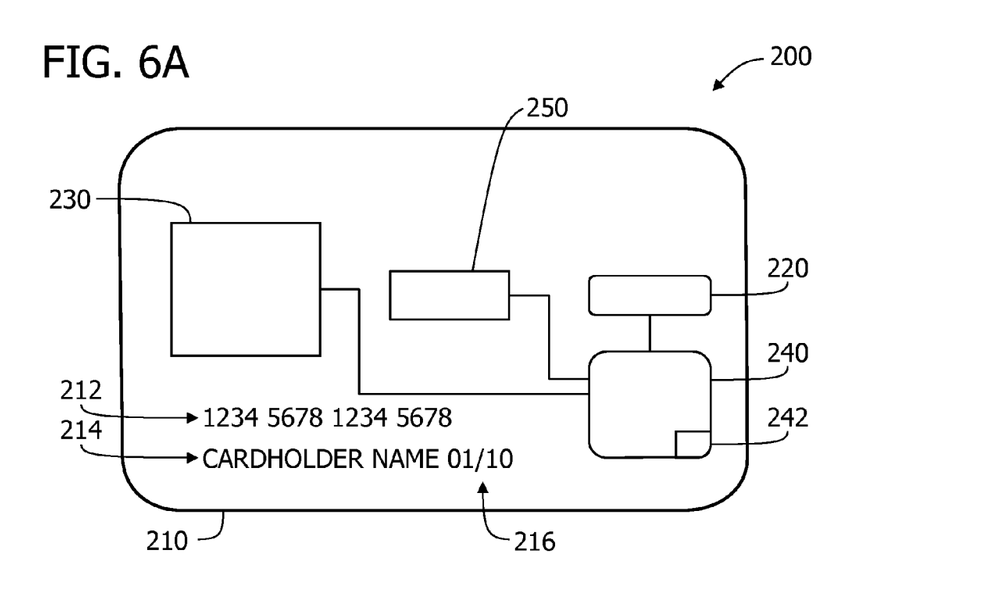
FIG. 6A is an illustration of an example fitness payment card configured to track fitness data of a cardholder that may be used as part of the system illustrated in FIG. 3.

FIG. 6A is an illustration of an example fitness payment card 200 for use by a consumer as part of an electronic payment transaction. For example, fitness payment card 200 may be used as part of payment card processing system 50 (shown in FIG. 1), as well as other variations of payment card transaction systems. In the example embodiment, fitness payment card 200 includes a flexible body 210. Typically, flexible body 210 is sized according to a standard, for example, standards promulgated by the International Organization for Standardization (ISO) and the International Electrotechnical Commission (IEC). More specifically, ISO/IEC 7810:2003 ID-1 specifies a size for payment cards of 85.60 mm by 53.98 mm. Additionally, ISO/IEC 7813 specifies that an ID-1 compliant payment card have a thickness of 0.76 mm and corners rounded with a radius of 3.18 mm. Although the ISO/IEC defines a standard size for payment cards, it is to be understood that the methods and systems described herein may be performed with a payment card of any shape or size that allows fitness payment card 200 to interact with POS terminal 115 (shown in FIG. 2) as described herein. Flexible body 210 may include indicia, for example, but not limited to, a payment card account number 212, a consumer account name 214, and an expiration date 216, displayed on flexible body 210 and/or embossed within flexible body 210.

In the example embodiment, fitness payment card 200 includes a wireless communication device 220, a fitness tracking component 230, and a processing device 240. In the example embodiment, wireless communication device 220, fitness tracking component 230, and processing device 240 are at least partially sealed within flexible body 210. In the example embodiment, processing device 240 is coupled to wireless communication device 220. In an alternative embodiment, wireless communication device 220 is included within processing device 240. Furthermore, processing device 240 may also include a memory device 242, or alternatively, may be coupled to memory device 242. The term processing device or processor, as used herein, refers to central processing units, microprocessors, microcontrollers, reduced instruction set circuits (RISC), application specific integrated circuits (ASIC), logic circuits, and any other circuit or processor capable of executing the functions described herein.

In the example embodiment, fitness tracking component 230 is coupled to processing device 240. In some embodiments, the fitness tracking component 230 is an accelerometer. The accelerometer(s) in the fitness payment card 200 may be of the common microelectromechanical (MEMS) type, having two variable capacitors formed by an arm or plate moveable between two fixed arms. Movement of the user device causes movement (due to its inertia) of the moveable plate, the amount of movement (velocity and/or acceleration) being measurable by the formed capacitors. One such arrangement in each of three orthogonal directions can give all three dimensions of movement, and assess different types of movement such as roll, pitch and yaw, rotation, and the like. The accelerometer(s) may alternatively be of the hot gas chamber-type known to the art.

The accelerometer in fitness payment card 200 acts a pedometer to count a number of steps taken by a cardholder. In the example embodiment, the accelerometer recognizes as a step a specific change in acceleration that would not be easily replicated by, for example, driving a car, in order that the count of number of steps taken is more accurate.

In other embodiments, the fitness tracking component 230 is a global positioning system (GPS). The GPS in the fitness payment card 200 includes or is in connection with the wireless communication device 220 that is configured to receive signals from a plurality of GPS satellites and to determine the a location of the GPS and the fitness payment card 200 using the signals. The GPS the location of the fitness payment card 200 and, therefore, the location of cardholder 58. In an example embodiment, the GPS is communicatively coupled to memory device 242 and is configured to store in memory device 242 the location of the fitness payment card 200 over a period of time.

Fitness payment card 200 may also include a power source 250 included within flexible body 210. Power source 250 may be coupled to wireless communication device 220, fitness tracking component 230, and/or processing device 240. In an embodiment, power source 250 is a battery. In an alternative embodiment, power source 250 is a capacitive storage device, although, power source 250 may be any suitable power source that is able to provide power to fitness payment card 200 so fitness payment card 200 can function as described herein.

Figure 6B:
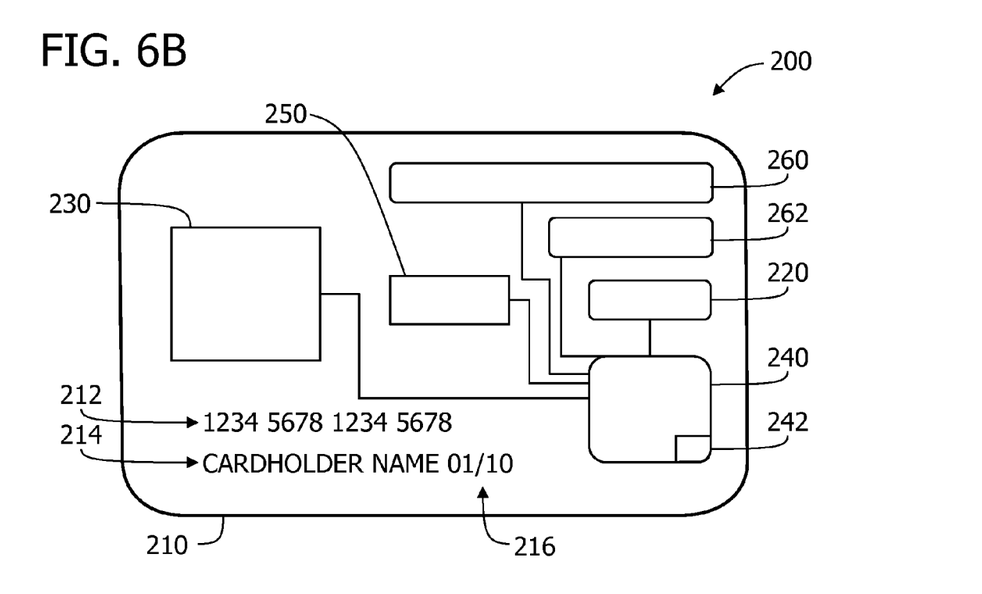
FIG. 6B is an illustration of another example fitness payment card configured to track fitness data of a cardholder and to display fitness data that may be used as part of the system illustrated in FIG. 3.

As shown in FIG. 6B, in other embodiments, fitness payment card 200 may include a digital display screen 260. Digital display screen 260 is coupled to processing device 240. In some embodiments, digital display screen 260 is a light emitting diode (LED) display screen, an organic light emitting diode (OLED) display screen, or any other suitable type of display screen that enables fitness payment card 200 to function as described herein. In some embodiments, processing device 240 provides digital display screen 260 with a signal, which is converted to a visual display by digital display screen 260. In some alternative embodiments, fitness payment card 200 may include multiple digital display screens, for example, first digital display screen 260 and a second digital display screen 262. Multiple display screens 260 and 262 may facilitate displaying more data than a single display screen.

As described above, payment card data may be provided to a POS terminal, for example, POS terminal 115, through the use of a wireless system. Wireless communication device 220 may be included within a radio frequency identification (RFID) communication system, a cellular communication system, a Bluetooth® communication system, or any other suitable communication system that allows fitness payment card 200 to function as described herein. In one embodiment, wireless communication device 220 of payment card 200 is an RFID device. RFID device 220 may be included as a portion of an RFID communication system (not shown in FIG. 6B). At least some known RFID communication systems include a transponder (i.e., RFID device 220) and a transceiver with a decoder, or a reader. The transponder typically includes a radio frequency (RF) integrated circuit, and an antenna positioned on a substrate, for example, flexible body 210. The antenna wirelessly receives RF energy from the reader and transmits the data encoded in the received RF energy to the RF integrated circuit.

RF readers utilize an antenna as well as a transceiver and decoder. In certain embodiments, when RFID device 220 passes through an electromagnetic zone of a reader, RFID device 220 is activated by the signal from the antenna. The reader decodes the data on the transponder and this decoded information is forwarded to a host computer for processing. In one embodiment, a reader, also referred to as an interrogator, is included within POS terminal 115 (shown in FIG. 2).

Several different types of transponders are utilized in RFID systems, including passive, semi-passive, and active transponders. Each type of transponder may be read only or read/write capable. Passive transponders obtain operating power from the RF signal of the reader that interrogates the transponder. Semi-passive and active transponders are powered by a battery, which generally results in a greater read range. Semi-passive transponders may operate on a timer and periodically transmit information to the reader. Transponders may also be activated when they are read or interrogated by a reader. Active transponders can initiate communication, whereas passive and semi-passive transponders are activated only when they are read by another device first.

Figure 7:
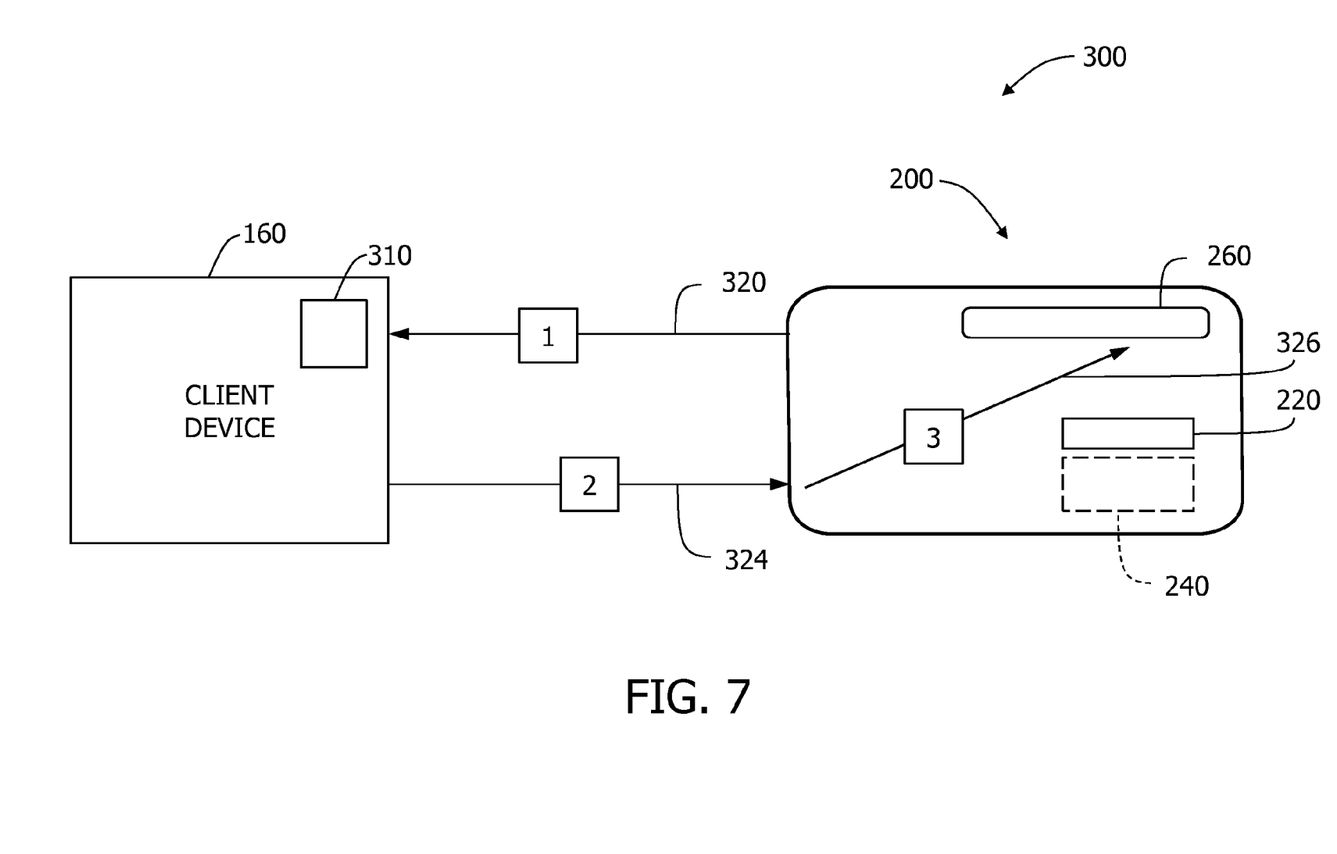
FIG. 7 is a data flow diagram illustrating data communication between the fitness payment card shown in FIGS. 6A and 6B and the client device shown in FIG. 4.

FIG. 7 is a data flow diagram 300 illustrating data communication between fitness payment card 200 (shown in FIGS. 6A and 6B) and client device 160 (shown in FIG. 4). More specifically, data flow diagram 300 illustrates data flow between merchant client device 160 and a payment card, for example, fitness payment card 200 of a cardholder such as cardholder 58 (shown in FIG. 1). In one embodiment, client device 160 includes a reader 310, for example, an RFID reader. Although described herein as an RFID reader, reader 310 may include a cellular receiver, a magnetic stripe reader, or any other type of device that allows payment card information to be entered into client device 160, for example a POS terminal 115 or a client system 114. In the example embodiment, when fitness payment card 200 is positioned within a predetermined distance from client device 160, power from reader 310 energizes RFID device 220. In response, RFID device 220 transmits 320 a signal to reader 310 that includes payment card identification information.

Payment card identification information may include, but is not limited to, a cardholder account number, a unique identifier, a cardholder's identification data, and an issuing bank's identification data. Client device 160 functions as described above and requests an authorization for a purchase entered into client device 160, for example, a POS terminal 115 or a client system 114, by, for example, merchant 70 or cardholder 74 (shown in FIG. 1). In addition, client device 160 can transmit 324 fitness tracking program data to payment card 200, which is provided 326 to digital display screen 260 for display. Alternatively, fitness tracking program data can be displayed on media output 168 of client device 160. In an alternative embodiment, client device 160 also transmits 324 an account identifier to payment card 200. The account identifier uniquely identifies the cardholder's account. Processing device 240 compares the account identifier to stored data to prevent fitness tracking program data associated with another account from being displayed on digital display screen 260 or on media output 168 of client device 160.

In one embodiment, a fitness data transfer message is sent, including the fitness data of the cardholder, and a fitness report is generated and, optionally, is displayed on fitness payment card 200 after a purchase is authorized. Alternatively, the fitness report is generated and, optionally, is displayed on client device 160. For example, issuing bank 56 may include the fitness report in an authorization response message, which is then provided for display on fitness payment card 200 or in client device 160. The fitness report may be displayed on digital display screen 260 or on media output 168 for a predetermined length of time, or until the next time a fitness report is generated and displayed. In another embodiment, the fitness report is displayed on digital display screen 260 prior to a payment transaction, upon a fitness tracking program request. Updating the fitness report displayed on digital display screen 260 may influence a cardholder's use of the payment card, for example, by providing a visual incentive for using the payment card. In another embodiment, the fitness report is displayed on client device 160 prior to a payment transaction, upon a fitness tracking program request. The fitness data transfer message may be generated at client device 160.

Figure 8:
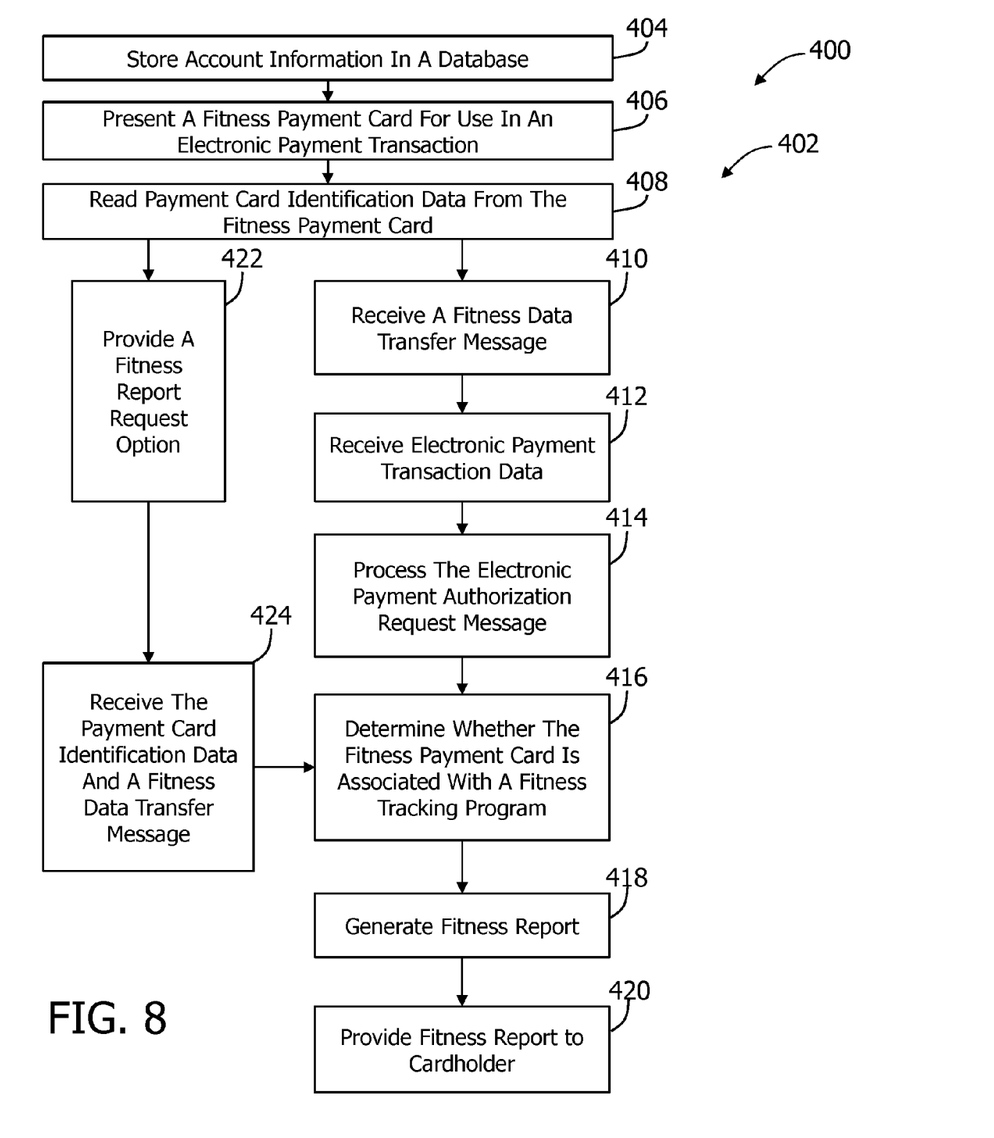
FIG. 8 is a flow diagram illustrating an example method for transmitting fitness data.

FIG. 8 is a flow diagram 400 illustrating an example method 402 for tracking fitness using a payment card, for example, fitness payment card 200 (shown in FIGS. 6A and 6B). In the example embodiment, method 402 includes storing 404 cardholder account information in a database, for example, database 120 (shown in FIG. 2). The cardholder account information may include, but is not limited to including, an issuing bank, a current balance, an available balance, fitness tracking program enrollment data, and fitness data and/or at least one fitness report associated with each issued payment card. The cardholder account information is associated with at least one payment card, for example, fitness payment card 200. The cardholder account information may include information related to pending transactions as well as cleared transactions. Cardholder account information may further include registration data for the fitness tracking program, wherein the registration data includes account identification information associated with the fitness payment card and the cardholder.

In the example embodiment, method 402 also includes presenting 406 a fitness payment card for use in an electronic payment card transaction (e.g., an electronic payment for goods or services and/or a request for a fitness tracking program update). For example, cardholder 58 (shown in FIG. 1) may present 406 fitness payment card 200 to merchant 54 and request an update on their fitness tracking report. Method 402 also includes reading 408 payment card identification information from fitness payment card 200. For example, merchant 54 may manually enter payment card identification information, or automatically read payment card identification information from fitness payment card 200 using, for example, POS terminal 115 (shown in FIG. 2).

In the example embodiment, method 402 includes receiving 410 a fitness data transfer message. For example, the fitness data transfer message may be sent from client device 160 to a fitness tracking computing device, for example, server 112 included in a payment network. In an example embodiment, the fitness data transfer message includes the payment card identification data, including registration data, associated with fitness payment card 200. For example, the fitness tracking computing device, for example, server 112 (shown in FIG. 2), may receive payment card identification data, including registration data, read from fitness payment card 200. As described above, registration data links the payment card to cardholder account information stored in database 120 and to the fitness tracking program. The registration data may include, for example, an account number, a unique identifier, a cardholder's identification data, and/or an issuing bank's identification data.

In the example embodiment, in addition to the payment card identification data, including registration data, electronic payment transaction data is also received 412 at fitness tracking computing device 113 after being sent from client device 160. For example, after deciding to make a purchase at merchant 54, cardholder 58 may present 406 fitness payment card 200 to merchant 54 as payment for the purchase. Electronic payment transaction data may include merchant identification data, a requested transaction payment amount, and/or data descriptive of the merchandise being purchased. In other words, client device 160 may transmit payment card identification data, including registration data, and the electronic payment transaction data to fitness tracking computing device 113. The combination of payment card identification data and electronic payment transaction data may also be referred to as an electronic payment authorization request message.

In the example embodiment, method 402 also includes processing 414 an electronic payment authorization request message. In the example embodiment, fitness tracking computing device 113 processes 414 an electronic payment authorization request message received from merchant 54 and determines an electronic payment authorization response. The electronic payment authorization response includes one of a payment acceptance and a payment denial, which is included within an electronic payment authorization response message. For example, when a credit card is offered as payment for a product or service, fitness tracking computing device 113, for example, server 112 determines if the cardholder account associated with the credit card has an available credit limit high enough to cover the requested electronic payment. Server 112 generates an electronic payment authorization response message in accordance with these determinations.

In the example embodiment, method 402 also includes determining 416 whether the offered payment card is associated with a fitness tracking program. As described above, the cardholder may be enrolled in a fitness tracking program. In the example embodiment, fitness tracking program enrollment data, i.e., registration data, is a type of account information that is stored in database 120. In the example embodiment, the fitness data transfer message includes an indicator, for example, an indicator flag and/or data within a particular field. The presence of the indicator informs a fitness tracking computing device, for example, server 112, that fitness payment card 200 may be registered in a fitness tracking program. The fitness tracking computing device 113 accesses the registration data stored in database 120 to determine 416 fitness tracking program enrollment.

In the example embodiment, method 402 also includes generating 418 a fitness report. The fitness report includes the fitness data. The fitness report may be included within an electronic payment authorization response message. The electronic payment authorization response message also includes either a payment authorization or a payment denial. Method 402 may also include providing 420 the fitness report to the cardholder. In one embodiment, the fitness report is transmitted from fitness tracking computing device 113 to POS terminal 115, and from POS terminal 115 to fitness payment card 200 for display on digital display screen 260. In one embodiment, POS terminal 115 indicates to the cardholder that a fitness report is available, and requests that the cardholder present the fitness payment card in order to receive the fitness report. As described above, data may be transmitted between POS terminal 115 and payment card 200 using a wireless system. Once the fitness report is received by fitness payment card 200, the fitness report may be displayed on digital display screen 260. In an alternative embodiment, the fitness report is transmitted from the fitness tracking computing device 113 to POS terminal 115, and from POS terminal 115 to client device 160, such as client system 114, for display on media output 168 of client device 160. In another embodiment, the fitness report is transmitted directly from fitness tracking computing device 113 to client device 160, for example, client system 114.

In an alternative embodiment, method 402 may include providing 422 a fitness report request option to the cardholder via a client device 160, for example, POS terminal 115. For example, POS terminal 115 may display a message instructing the cardholder to press a key on a POS terminal keypad if the cardholder would like to receive a fitness report. Method 402 also includes receiving 424, at POS terminal 115, the payment card identification data, including registration data, and a fitness data transfer message at a fitness tracking computing device 113. Upon selection of the fitness report request option, POS terminal 115 generates the fitness data transfer message and transmits the payment card identification data, including registration data, and the fitness data transfer message to the fitness tracking computing device 113.

The methods and systems described herein facilitate providing a fitness report, for example, to a fitness payment card for display on the fitness payment card, upon a cardholder request. In an example embodiment, the cardholder presents 406 the fitness payment card for use in an electronic payment transaction (e.g., a request for a fitness report). The payment card identification data, including registration data, is read 408 by POS terminal 115 and the cardholder selects a fitness report request option provided 422 by POS terminal 115. The payment card identification data and the fitness data transfer message are received 424 at the fitness tracking computing device 113. As described above, the fitness tracking computing device 113 then determines 416 whether the fitness payment card is associated with a fitness tracking program and generates 418 a fitness report. The fitness report is provided 420 to the cardholder, for example, for display on the fitness payment card 200 digital display screen 260 or for display on client device 160.

Figure 9:
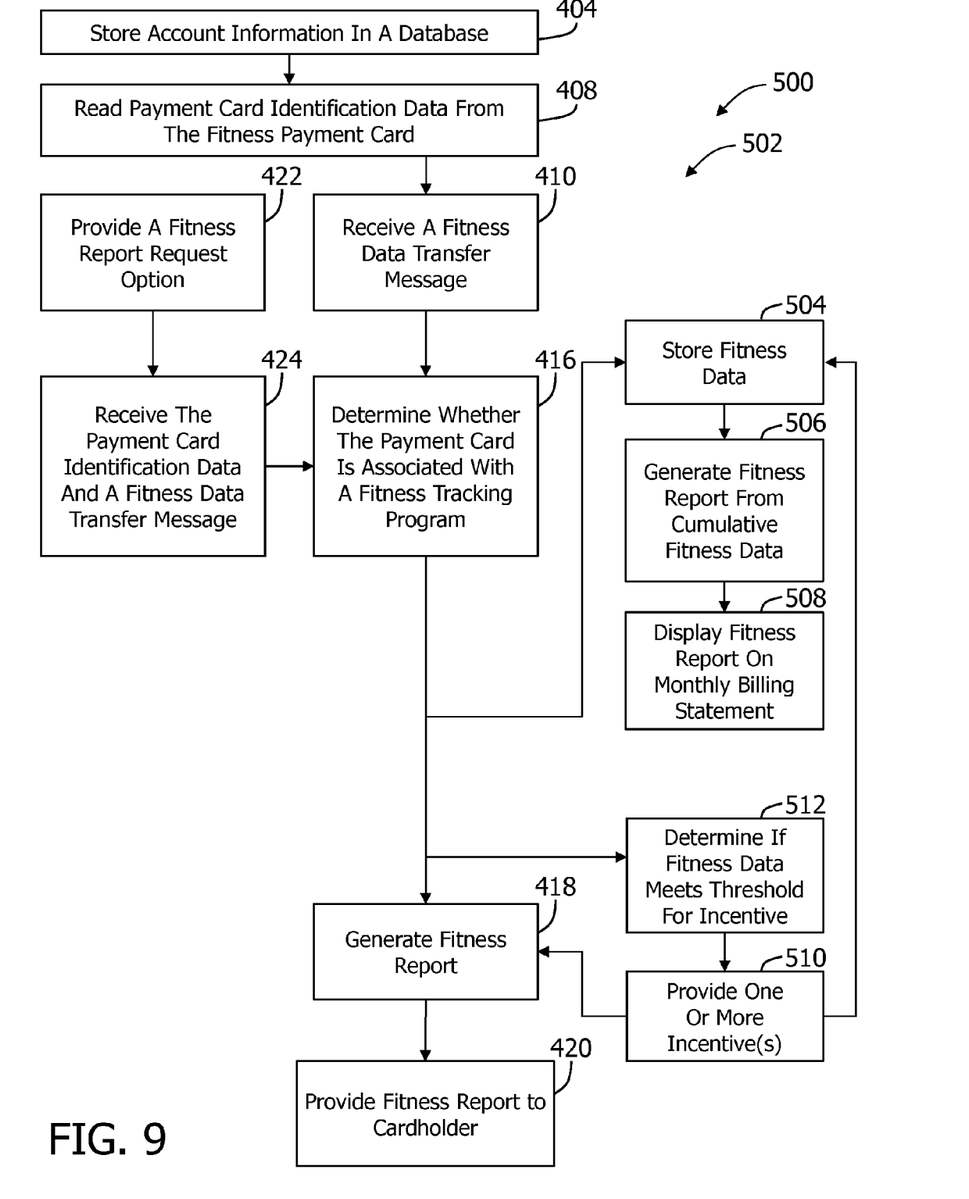
FIG. 9 is a flow diagram illustrating an example method for transmitting fitness data without requiring a transaction.

FIG. 9 is a flow diagram 500 illustrating an example method 502 for tracking fitness using a payment card, for example, fitness payment card 200 (shown in FIGS. 6A and 6B). In the example embodiment, the fitness tracking program that the cardholder is enrolled in offers an incentive to the cardholder based on the fitness report. For example, the fitness tracking program may reward a cardholder for taking a threshold number of steps or travelling a threshold distance. In one embodiment, a cardholder travels a threshold distance and is awarded an incentive. The incentive can be at least one of, for example, a coupon, at least one rewards point(s) that can be redeemed for goods and services or can be exchanged for cash back, or an advertisement from a participating merchant. For example, a cardholder can travel a threshold distance that marks the cardholder as an "active" cardholder, and the fitness tracking program can provide the active cardholder a coupon to a participating sporting goods store. Alternatively, the fitness report may report a certain route summary that identifies a route frequently travelled by the cardholder, and the fitness tracking program may provide the cardholder with an advertisement or coupon for a participating merchant located along or near to the route frequently travelled by the cardholder. Alternatively, a cardholder may take a threshold number of steps that identifies the cardholder as an "active" cardholder, and the fitness tracking program may award the active cardholder with at least one rewards point(s). In some embodiments, the number of rewards points awarded may be proportional to the number of steps taken or the number of miles travelled.

In some embodiments, the cardholder may be able to "opt in" to receiving one or multiple type(s) of incentive(s). For example, a cardholder may choose to only receive rewards points, may only choose to receive coupons, or may choose both.

In one embodiment, method 502 may include displaying 508 a fitness report on the monthly billing statement of the cardholder. The fitness report may include one or more incentives, as described above. Method 502 may include storing 504 the fitness data in database 120. The cumulative fitness data is stored in database 120. Method 502 can further include displaying 508 a fitness report on the monthly billing statement, wherein the fitness report is generated 506 from the cumulative fitness data.

Alternatively, method 402 may include providing 510 one or more incentives upon authorization of an electronic payment transaction. For example, if the electronic payment authorization request message is approved, and cardholder is enrolled with the fitness tracking program associated with fitness payment card 200, fitness tracking computing device 113 may determine 512 if the fitness data meets a threshold value. The fitness tracking computing device then facilitates providing 510 the one or more incentive to the cardholder, for example, by providing 510 to POS terminal 115, and transmitting from POS terminal 115 to client device 160 for display on media output 168 of client device 160.

In the example embodiment described above, fitness tracking computing device 113 is described as performing many steps of method 402 and of method 502. Fitness tracking computing device may be in communication with or integral to server 112 of a payment network. In the example embodiment, server 112 is associated with issuer 56 (shown in FIG. 1). In alternative embodiments, server 112 is associated with interchange network 62, merchant bank 60, or any other party involved in multi-party payment card industry system 52 (shown in FIG. 1). Furthermore, various steps of method 402 may be performed by different parties. For example, issuer 56 may process 414 an electronic payment authorization request message and transmit an electronic payment authorization response message to interchange network 62. In other alternative embodiments, server 112 is associated with a transaction processor, or any other party involved in a payment card processing system (shown in FIG. 2).

In one embodiment, the fitness report displayed on payment card digital display screen 260 includes a number of steps taken by the cardholder. In an alternative embodiment, digital display screen 260 is capable of displaying more than one value corresponding to fitness report. Alternatively, fitness payment card 200 may include more than one display screen, for example, digital display screens 260 and 262 (shown in FIGS. 6A and 6B). In the alternative embodiment, digital display screen 260 is configured to display the number of steps taken and digital display screen 262 is configured to display a total distance travelled by the cardholder. By displaying more than one value, more information can be presented to the cardholder.

In another alternative embodiment, periodically or upon request, fitness tracking computing device 113 facilitates transmitting the fitness report via long range communication, for example, but not limited to, cellular communications and radio transmissions, in order to update the information stored in database 120, to be displayed on client device 160, and/or to be displayed on fitness payment card 200.

In yet another embodiment, a cardholder can participate passively in a competition between other cardholders enrolled in the fitness tracking program. More specifically, upon receiving the fitness data of the cardholder in the database 120 and the competitor fitness data of at least one competitor cardholder, a fitness tracking computing device 113 generates a comparison of the fitness data of the cardholder with the competitor fitness data. The fitness tracking computing device 113 determines a fitness score associated with the cardholder based on the comparison. The fitness score is included, for example, in the fitness report. In other embodiments, an incentive is provided to the cardholder based on the fitness score, wherein the incentive includes, for example, at least one of a coupon, a reward points, and an advertisement.

Furthermore, data transmitted wirelessly using the methods and systems described herein is encrypted and conforms to a protocol that is consistent with capabilities of the fitness payment card and the client device, for example, a POS terminal. The encryption facilitates preventing communication between the payment card and a POS terminal that is either unknown to the cardholder or not approved by the cardholder.

As will be appreciated based on the foregoing specification, the above-described embodiments of the disclosure may be implemented using computer programming or engineering techniques including computer software, firmware, hardware or any combination or subset thereof, wherein the technical effect of the systems and processes described herein is achieved by creating a network-based system for tracking fitness of a cardholder. The technical effect is also achieved with a method for tracking fitness of a cardholder. Any such resulting program, having computer-readable code means, may be embodied or provided within one or more computer-readable media, thereby making a computer program product, i.e., an article of manufacture, according to the discussed embodiments of the disclosure. The computer-readable media may be, for example, but is not limited to, a fixed (hard) drive, diskette, optical disk, magnetic tape, semiconductor memory such as read-only memory (ROM), and/or any transmitting/receiving medium such as the Internet or other communication network or link. The article of manufacture containing the computer code may be made and/or used by executing the code directly from one medium, by copying the code from one medium to another medium, or by transmitting the code over a network.

The above-described embodiments of methods and system tracking fitness of a cardholder provide a cost-effective and reliable means for tracking fitness of a cardholder. More specifically, the methods and systems described herein provide a cardholder with an up-to-date fitness report. Furthermore, the methods and systems described herein may facilitate increasing usage of the payment card by providing an attractive differentiation from other payment cards.

This written description uses examples to disclose the embodiments, including the best mode, and also to enable any person skilled in the art to practice the disclosure, including making and using any devices or systems and performing any incorporated methods. The patentable scope of the embodiments is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A computer-implemented method for tracking fitness data of a cardholder using a fitness payment card and a fitness tracking computing device in communication with a memory, said method comprising:
    storing registration data within the memory, wherein the registration data includes an account identifier associated with the fitness payment card and the cardholder;
    receiving, by the fitness tracking computing device, a fitness data transfer message that includes the registration data and the fitness data of the cardholder, wherein the fitness data is collected by the fitness payment card;
    determining that the fitness payment card is registered in a fitness tracking program based on the registration data;
    electronically generating a fitness report including at least the fitness data of the cardholder; and
    providing the fitness report to the cardholder, wherein the fitness report is displayed on the fitness payment card.

2. The computer-implemented method of claim 1, wherein providing the fitness report to the cardholder further comprises facilitating display of the fitness report on at least one of:
    a monthly billing statement of the cardholder; and
    a client device.

3. The computer-implemented method of claim 1, wherein the fitness data comprises at least one of a number of steps taken by the cardholder, a distance travelled by the cardholder, and a route summary including locations travelled by the cardholder.

4. The computer-implemented method of claim 1, wherein the fitness tracking computing device is associated with at least one of a merchant, a merchant bank, an interchange network, and a payment card issuer.

5. The computer-implemented method of claim 4, further comprising:
    receiving, in response to a transaction by the cardholder, the fitness data transfer message, including the fitness data, and an electronic payment authorization request message associated with the transaction that includes transaction data, wherein transaction data includes at least one of merchant identification data, a requested transaction payment amount, and data descriptive of a purchase type;
    processing the electronic payment authorization request message including the transaction data; and
    receiving a payment authorization response message that includes at least one of a payment authorization and a payment denial.

6. The computer-implemented method of claim 5, wherein processing the electronic payment authorization message includes:
    parsing the electronic payment authorization request message from the fitness data transfer message; and
    storing the fitness data in the memory.

7. The computer-implemented method of claim 5, wherein the electronic payment authorization request message includes the fitness data transfer message.

8. The computer-implemented method of claim 1, further comprising providing an incentive to the cardholder based at least in part on the fitness report, wherein the incentive includes at least one of a coupon, at least one reward points, and an advertisement.

9. The computer-implemented method of claim 1, further comprising:
    receiving, by the fitness tracking computing device, competitor fitness data of at least one competitor cardholder;
    generating a comparison of the fitness data of the cardholder with the competitor fitness data; and
    determining a fitness score of the cardholder based on the comparison, wherein the fitness report further includes the fitness score.

10. A computer system for tracking fitness data of a cardholder, the computer system comprising:
    a memory; and
    a fitness tracking computing device configured to:
    store registration data within the memory, wherein the registration data includes an account identifier associated with a fitness payment card and the cardholder;
    receive a fitness data transfer message that includes the registration data and the fitness data of the cardholder, wherein the fitness data is collected by the fitness payment card;
    determine that the fitness payment card is registered in a fitness tracking program based on the registration data;
    electronically generate a fitness report including at least the fitness data of the cardholder; and
    provide the fitness report to the cardholder, wherein the fitness report is displayed on the fitness payment card.

11. The computer system of claim 10, wherein the fitness tracking computing device is further configured to facilitate display of the fitness report on at least one of:
    a monthly billing statement of the cardholder; and
    a client device.

12. The computer system of claim 10, wherein the fitness data comprises at least one of a number of steps taken by the cardholder, a distance travelled by the cardholder, and a route summary including locations travelled by the cardholder.

13. The computer system of claim 10, wherein the fitness tracking computing device is associated with at least one of a merchant, a merchant bank, an interchange network, and a payment card issuer.

14. The computer system of claim 13, wherein the fitness tracking computing device is further configured to:
    receive, in response to a transaction by the cardholder, an electronic payment authorization request message associated with the transaction that includes data from the fitness data transfer message and transaction data, wherein transaction data includes at least one of merchant identification data, a requested transaction payment amount, and data descriptive of a purchase type;
process the electronic payment authorization request message including the transaction data; and
receive a payment authorization response message that includes at least one of a payment authorization and a payment denial.

15. The computer system of claim 14, wherein the fitness tracking computing device is further configured to:
parse the electronic payment authorization request message from the fitness data transfer message; and
store the fitness data in the memory.

16. The computer system of claim 14, wherein the electronic payment authorization request message includes the fitness data transfer message.

17. The computer system of claim 10, wherein the fitness tracking computing device is further configured to provide an incentive to the cardholder based at least in part on the fitness report, wherein the incentive includes at least one of a coupon, at least one reward points, and an advertisement.

18. The computer system of claim 10, wherein the fitness tracking computing device is further configured to:
receive competitor fitness data of at least one competitor cardholder;
generate a comparison of the fitness data of the cardholder with the competitor fitness data; and
determine a fitness score of the cardholder based on the comparison, wherein the fitness report includes the fitness score.

* * * * *